(12) United States Patent
Humble et al.

(10) Patent No.: US 11,093,904 B2
(45) Date of Patent: Aug. 17, 2021

(54) COGNITIVE SCHEDULING PLATFORM

(71) Applicant: International Business Machines Corporation, Armonk, NY (US)

(72) Inventors: James Humble, Yorktown Heights, NY (US); James R. Kozloski, Yorktown Heights, NY (US); Clifford A. Pickover, Yorktown Heights, NY (US); Tim Rumbell, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 268 days.

(21) Appl. No.: 15/841,764

(22) Filed: Dec. 14, 2017

(65) Prior Publication Data
US 2019/0188650 A1 Jun. 20, 2019

(51) Int. Cl.
*G06Q 10/10* (2012.01)
*G06K 9/00* (2006.01)
*G06Q 10/06* (2012.01)

(52) U.S. Cl.
CPC ..... *G06Q 10/1097* (2013.01); *G06K 9/00335* (2013.01); *G06Q 10/063116* (2013.01)

(58) Field of Classification Search
None
See application file for complete search history.

(56) References Cited

U.S. PATENT DOCUMENTS

| 5,247,438 | A | 9/1993 | Subas et al. |
| 6,505,167 | B1 * | 1/2003 | Horvitz ............ G06Q 10/06314 705/7.21 |
| 7,728,214 | B2 * | 6/2010 | Oliver .................. A61B 5/0006 84/612 |
| 7,831,679 | B2 * | 11/2010 | Apacible ............... H04W 40/02 340/4.3 |

(Continued)

FOREIGN PATENT DOCUMENTS

| WO | WO-2015200153 A1 * | 12/2015 | .............. H04W 8/18 |
| WO | WO 2016/012957 A1 | 1/2016 | |

(Continued)

OTHER PUBLICATIONS

Ghandeharioun, Asma, et al. "Towards understanding emotional intelligence for behavior change chatbots." 2019 8th International Conference on Affective Computing and Intelligent Interaction (ACII). IEEE, 2019. (Year: 2019).*

(Continued)

*Primary Examiner* — Matthew S Gart
*Assistant Examiner* — Derick J Holzmacher
(74) *Attorney, Agent, or Firm* — Anthony Curro, Esq.; McGinn I.P. Law Group, PLLC

(57) ABSTRACT

A time-management planning method, system, and computer program product, includes determining at least one of a cognitive state and a contextual state of a user, compiling a specification of a cognitive goal associated with accomplishing a scheduled task for a period of time, and performing a planning action, via a time management software platform, to adjust the scheduled task based on the specification of the cognitive goal and the at least one of the cognitive state and the contextual state of the user.

13 Claims, 4 Drawing Sheets

(56) References Cited

U.S. PATENT DOCUMENTS

| | | | |
|---|---|---|---|
| 7,914,419 B2* | 3/2011 | Karkanias | A63B 24/0062 482/8 |
| 7,996,338 B2* | 8/2011 | Kamar | G06Q 10/109 706/11 |
| 8,020,104 B2* | 9/2011 | Robarts | G06F 1/163 715/744 |
| 8,562,354 B2 | 10/2013 | Groot et al. | |
| 8,917,580 B2 | 12/2014 | Cedeno | |
| 8,930,290 B2 | 1/2015 | Cragun et al. | |
| 9,131,887 B2* | 9/2015 | Sato | A61B 5/165 |
| 9,164,656 B1* | 10/2015 | Keller | G16H 40/20 |
| 2004/0003042 A1* | 1/2004 | Horvitz | G06Q 10/109 709/204 |
| 2007/0113725 A1* | 5/2007 | Oliver | A61B 5/02438 84/612 |
| 2007/0113726 A1* | 5/2007 | Oliver | A61B 5/0006 84/615 |
| 2007/0118043 A1* | 5/2007 | Oliver | A61B 5/0245 600/519 |
| 2007/0300225 A1* | 12/2007 | Macbeth | G06Q 10/10 718/100 |
| 2008/0004926 A1* | 1/2008 | Horvitz | G06Q 10/047 705/7.26 |
| 2008/0005055 A1* | 1/2008 | Horvitz | G06Q 10/04 706/62 |
| 2008/0300109 A1* | 12/2008 | Karkanias | A63B 24/0062 482/8 |
| 2010/0082376 A1* | 4/2010 | Levitt | G06Q 10/06311 705/7.18 |
| 2010/0169134 A1* | 7/2010 | Cheng | G06Q 10/06398 705/7.42 |
| 2012/0130196 A1* | 5/2012 | Jain | A61B 5/681 600/300 |
| 2012/0130201 A1* | 5/2012 | Jain | A61B 5/08 600/301 |
| 2012/0130202 A1* | 5/2012 | Jain | A61B 5/4848 600/301 |
| 2012/0197621 A1* | 8/2012 | Jain | G16H 50/50 703/11 |
| 2012/0197622 A1* | 8/2012 | Jain | G16H 50/20 703/11 |
| 2012/0289790 A1* | 11/2012 | Jain | G16H 40/67 600/301 |
| 2012/0289791 A1* | 11/2012 | Jain | A61B 5/02055 600/301 |
| 2012/0289792 A1* | 11/2012 | Jain | A61B 5/165 600/301 |
| 2012/0289793 A1* | 11/2012 | Jain | A61B 5/0022 600/301 |
| 2012/0289794 A1* | 11/2012 | Jain | A61B 5/165 600/301 |
| 2012/0290266 A1* | 11/2012 | Jain | G16H 50/50 702/187 |
| 2013/0091453 A1* | 4/2013 | Kotler | G06Q 30/0209 715/772 |
| 2014/0067455 A1* | 3/2014 | Zhang | G06Q 10/109 705/7.24 |
| 2014/0278678 A1 | 9/2014 | Malkin et al. | |
| 2015/0112899 A1* | 4/2015 | Dagum | G16H 50/20 706/12 |
| 2015/0140527 A1* | 5/2015 | Gilad-Barach | A61B 5/165 434/236 |
| 2015/0178689 A1 | 6/2015 | Marcotte | |
| 2016/0063874 A1* | 3/2016 | Czerwinski | G09B 5/06 434/236 |
| 2016/0117948 A1* | 4/2016 | Kraemer | G09B 19/00 434/236 |
| 2016/0232137 A1* | 8/2016 | Liu | G06Q 10/107 |
| 2016/0267809 A1* | 9/2016 | deCharms | A61B 3/113 |
| 2017/0039480 A1* | 2/2017 | Bitran | G06F 19/3481 |
| 2017/0100066 A1* | 4/2017 | Delaney | A61B 5/165 |
| 2017/0178048 A1* | 6/2017 | Ghotbi | G06Q 10/063114 |
| 2017/0200133 A1* | 7/2017 | Werner | G06Q 10/0633 |
| 2018/0374000 A1* | 12/2018 | Herzig | G06N 20/00 |
| 2019/0205839 A1* | 7/2019 | Dotan-Cohen | A61B 5/1118 |
| 2019/0274632 A1* | 9/2019 | Kochura | A61B 5/165 |
| 2020/0114207 A1* | 4/2020 | Weldemariam | A63B 24/0075 |
| 2020/0220828 A1* | 7/2020 | Kwatra | G06F 16/337 |
| 2020/0220933 A1* | 7/2020 | Kwatra | H04L 67/22 |
| 2020/0265118 A1* | 8/2020 | Rofrano | G06F 8/60 |
| 2020/0265829 A1* | 8/2020 | Liu | G10L 13/033 |
| 2020/0372367 A1* | 11/2020 | Ha | G06N 3/088 |
| 2021/0056167 A1* | 2/2021 | Lam | G06Q 50/01 |
| 2021/0081813 A1* | 3/2021 | Cecchi | H04L 9/0643 |

FOREIGN PATENT DOCUMENTS

| | | | | |
|---|---|---|---|---|
| WO | WO-2016004396 A1 * | 1/2016 | | G09B 19/00 |
| WO | WO-2016118435 A1 * | 7/2016 | | G10L 15/1822 |

OTHER PUBLICATIONS

Tellols, Dolça, et al. "Enhancing sentient embodied conversational agents with machine learning." Pattern Recognition Letters 129 (2020): 317-323. (Year: 2020).*

Thosar, D. S., et al. "Review on Mood Detection using Image Processing and Chatbot using Artificial Intelligence." life 5.03 (2018). (Year: 2018).*

Abbas, Tahir, et al. "Crowd of Oz: a crowd-powered social robotics system for stress management." Sensors 20.2 (2020): 569. (Year: 2020).*

Radziwill, Nicole M., and Morgan C. Benton. "Evaluating quality of chatbots and intelligent conversational agents." arXiv preprint arXiv:1704.04579 (2017). (Year: 2017).*

Mel, et al. "The NIST Definition of Cloud Computing". Recommendations of the National Institute of Standards and Technology. Nov. 16, 2015.

K. Myers et al., "An Intelligent Personal Assistant for Task and Time Management," AI Magazine, vol. 28, No. 2, 2007, pp. 47-61.

Y. Gil et al., "Capturing common knowledge about tasks: Intelligent assistance for to-do lists," ACM Transactions on Interactive Intelligent Systems (TiiS), vol. 2, No. 3, 2012, article 15, 35 pages.

* cited by examiner

COGNITIVE SCHEDULING PLATFORM

TECHNICAL FIELD

The present invention relates generally to a system, method, and computer program product for a cognitive scheduling platform.

BACKGROUND

Conventionally; scheduling software (e.g., calendar software) requires a user to manually input time allocated and does not dynamically update in accordance with a user's fluctuating activities and other aspects of a user's profile.

The inventors have recognized a problem in the art that the problem of scheduling time to perform tasks that are required for an individual to advance a long term goal, solve a difficult problem, or otherwise have a work context present for sufficient time to accomplish the task (for example, working on a piece of software code) are not considered in conventional scheduling software. Thus, the conventional scheduling software are inefficient.

SUMMARY

In an exemplary embodiment, the present invention can provide a computer-implemented time-management planning method, the method including determining at least one of a cognitive state and a contextual state of a user, compiling a specification of a cognitive goal associated with accomplishing a scheduled task for a period of time, and performing a planning action, via a time management software platform, to adjust the scheduled task based on the specification of the cognitive goal and the at least one of the cognitive state and the contextual state of the user.

On or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
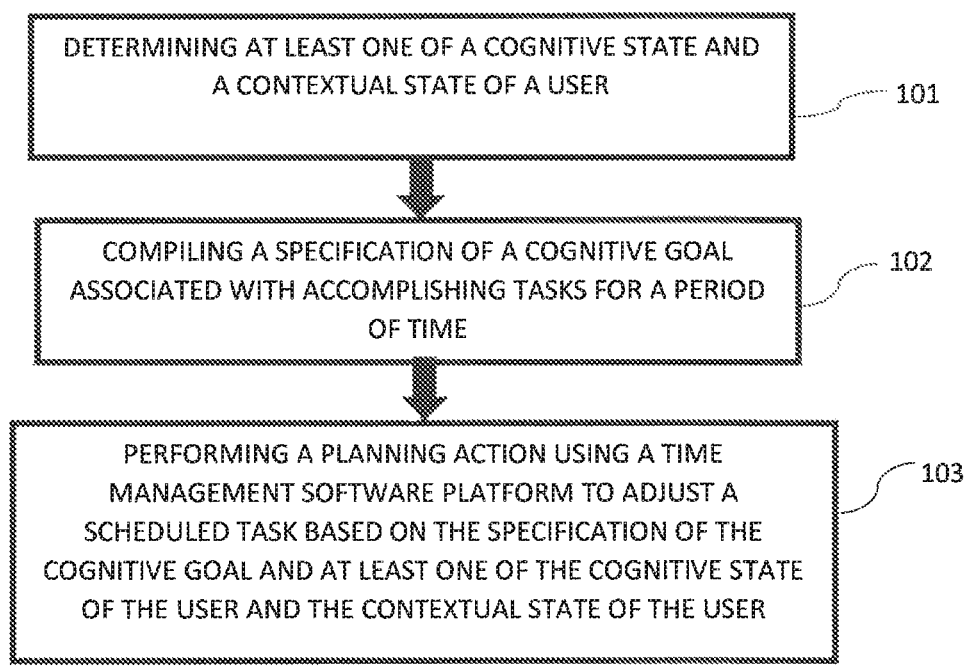
FIG. 1 exemplarily shows a high-level flow chart for a time-management planning method 100 according to an embodiment of the present invention.

The invention will now be described with reference to FIGS. 1-4, in which like reference numerals refer to like parts throughout. It is emphasized that, according to common practice, the various features of the drawing are not necessarily to scale. On the contrary the dimensions of the various features can be arbitrarily expanded or reduced for clarity.

By way of introduction of the example depicted in FIG. 1, an embodiment of a time-management planning method 100 according to the present invention can include various steps for creating an agent to compete on behalf of the user for his or her time to perform tasks by insisting that the individual schedule the appropriate amount of time of performing each of the tasks. In doing so, the invention can provide a time estimate for accomplishing progress on particular ongoing tasks, objectives, and projects of which only the individual user is aware, ranks the value of these efforts on a priority scale, schedules the necessary time to advance these projects on future calendar entries, compares the priority of incoming demands on the individuals time in the form of calendar entries against the existing "protected time" for the projects, and reschedules the individual's "protected time" if it's priority is superseded by an incoming calendar request.

Figure 2:
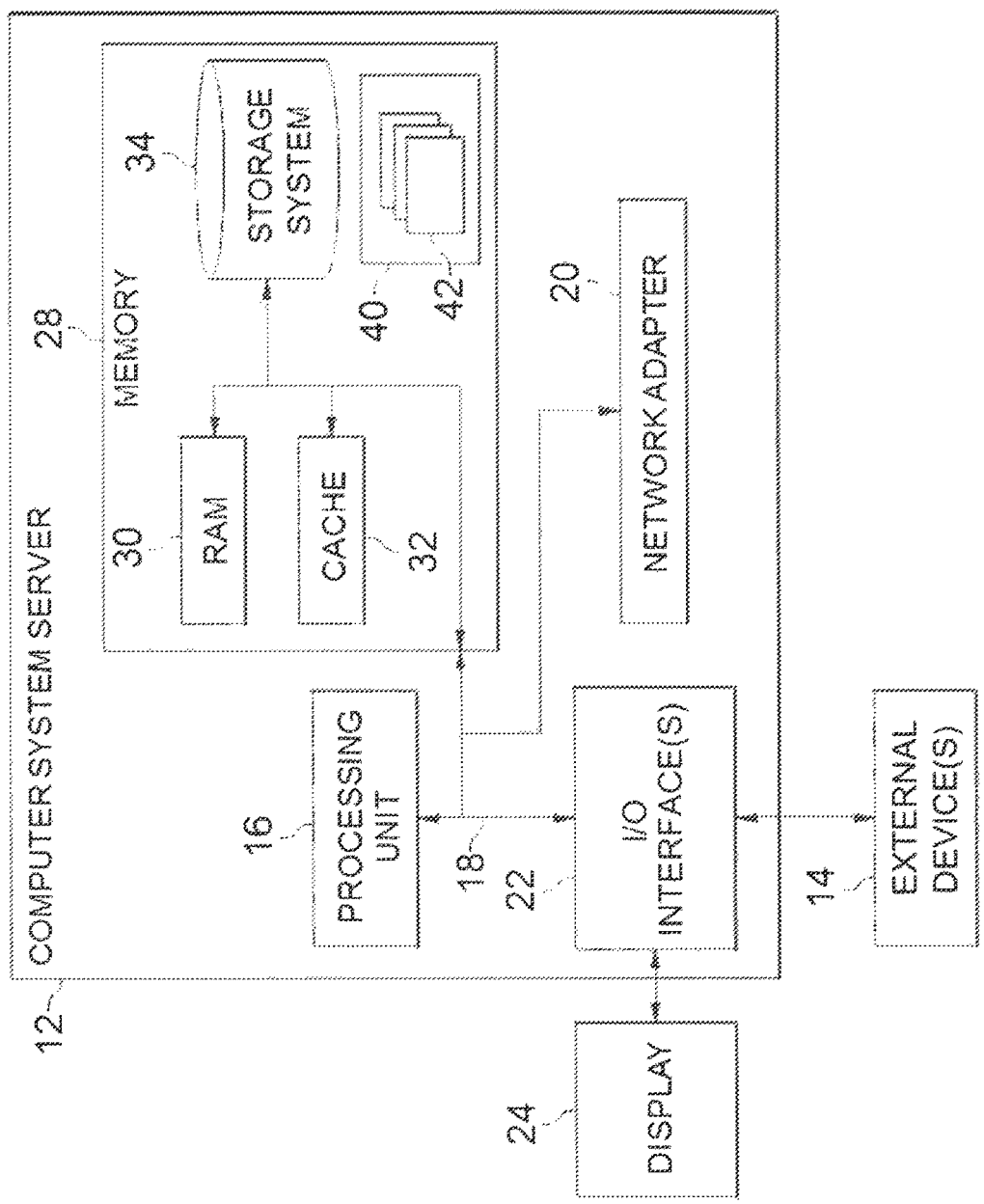
FIG. 2 depicts a cloud-computing node 10 according to an embodiment of the present invention.

By way of introduction of the example depicted in FIG. 2, one or more computers of a computer system 12 according to an embodiment of the present invention can include a memory 28 having instructions stored in a storage system to perform the steps of FIG. 1.

Thus, a time-management planning method 100 according to an embodiment of the present invention may act in a more sophisticated, useful and cognitive manner, giving the impression of cognitive mental abilities and processes related to knowledge, attention, memory, judgment and evaluation, reasoning, and advanced computation. In other words, a "cognitive" system can be said to be one that possesses macro-scale properties—perception, goal-oriented behavior, learning memory and actions generally recognized as cognitive.

Although one or more embodiments may be implemented in a cloud environment 50 (see e.g., FIG. 3), it is nonetheless understood that the present invention can be implemented outside of the cloud environment.

Referring generally to the method of FIG. 1, the intervention of the cognitive agent to schedule daily tasks on behalf of the user results in several major benefits over an individual scheduling their own daily activities. For example, improved productivity for the individual, by removing the cognitive load associated with balancing work load among many competing, long range tasks. Also, improved confidence in the individual that the daily tasks selected have been appropriately prioritized by the cognitive agent, and are the best use of the individual's current time in terms of achieving both productivity and cognitive goals. This allows the individual to simply 'get to work', without wondering if there is something more important for the individual to be doing. Moreover, potentially many weeks or months of time will have been allocated for protected tasks in advance, with the cognitive agent reallocating time as needed when conflicting, high-priority calendar entries arrive, making a user aware of the nature of the work and general workload over coming weeks and months.

The method 100 also includes steps for solving the problem of the various contexts that an individual may find themselves working in on a daily basis. The cognitive agent is context aware, and can incorporate information about location, time of day, recent/predicted future activities, health-related information such as amount of sleep in recent nights, amount of recent exercise, physical environment (e.g. sitting in a self driving car, sitting in the office, etc.). social environment (e.g. alone, around other people), etc. This context can be associated with prior knowledge of both task-related productivity and performance, and moods and mood outcomes. The method 100 can predict or expect particular contexts based on existing calendar entries, routine of the user, etc. The tasks scheduled for each upcoming day can therefore be balanced with appropriate tusks to achieve maximal progress at 'deadline' tasks and 'protected time' tasks, while aiming for the mood outcomes that move the user in the direction of the specified cognitive goal, given the array of contexts expected on that day.

In addition, the method considers the cognitive state of the user. Cognitive states are defined as functions of measures of a user's total behavior collected over some period of time from at least one personal information collector (including musculoskeletal gestures, speech gestures, eye movements, internal physiological changes, measured by imaging circuits, microphones, physiological and/or kinematic sensors in a high dimensional measurement space) within a lower dimensional feature space. In one exemplary embodiment, certain feature extraction techniques are used for identifying certain cognitive and emotional traits. Specifically, the reduction of a set of behavioral measures over some period of time to a set of feature nodes and vectors, corresponding to the behavioral measures' representations in the lower dimensional feature space, is used to identify the emergence of certain cognitive state(s) over that period of time. One or more exemplary embodiments use certain feature extraction techniques for identifying certain cognitive states. The relationship of one feature node to other similar nodes through edges in a graph corresponds to the temporal order of transitions from one set of measures and the feature nodes and vectors to another. Some connected subgraphs of the feature nodes are herein also defined as a cognitive state. The present application also describes the analysis, categorization, and identification of these cognitive states of further feature analysis of subgraphs, including dimensionality reduction of the subgraphs, for example by graphical analysis, which extracts topological features and categorizes the resultant subgraph and its associated feature nodes and edges within a subgraph feature space.

The cognitive state can include, and not limited to, a cohort condition such as autism, attention-deficit disorder (ADD), attention-deficit hyperactivity disorder (ADHD), Asperger's syndrome, etc. and a cognitive level such as inebriation, fatigue, stress, distraction level, etc.

That is, in step 101, at least one of a cognitive state and a contextual state of the user is determined.

In step 102, a specification of a cognitive goal associated with accomplishing a task for a period of time is compiled. The cognitive goal may be any of, for example, a sense of accomplishment, sense of peace, a sense of de-complexifying the complexities of life, receiving kudos from a boss, being able to sleep at night, etc. The specification an be a digital profile in some digital format consumable by some time management software platform.

The specification is any of, for example, a manual (e.g., through an explicitly request by a user or a third party) or inferred (e.g., the software estimates a user would like to have a certain mood outcome). This may (optionally) be based on assessing how stressed a user is.

In step 103, a planning action is performed using, for example, a time management software platform to adjust a scheduled task (e.g., move the task, change a time allotted for the task, change who performs the task, etc.) based on the specification of the cognitive goal and at least one of the cognitive state and contextual state of the user.

The planning action is performed by, for example, providing a time estimate for accomplishing progress on particular ongoing tasks, objectives, and projects that only the individual user is aware of, ranking the value of these efforts on a priority scale, scheduling the necessary time to advance these projects on future calendar entries, comparing the priority of incoming demands on the individuals time in the form of calendar entries against the existing "protected time" for the projects, and reschedules the individual's "protected time" if its priority is superseded by an incoming calendar request. The time estimate can be learnt from past estimates of similar activities either from the same user or from a cohort of users. For example, a user with a similar intelligence level and cognitive profile would be allotted similar time.

The time management software platform may "nag" a user, using natural language processing, a chatbot, etc. as an action. The planning action may be recommending, specifying, ordering, or marking a set of to-dos in a specified limited window of time. The planning action may be selected to be performed in an environment that includes any of: calendar software, planner software, project planning apps, a virtual world, etc.

The cognitive goal may include an anticipated cognitive state of others (e.g., not just the user), teams, organizations, departments, family members, etc. Furthermore, the system does not have to be limited to organizing a single user's projects/tasks. For example, when organizing a team's or organizations projects whereby many users/employees can complete the same task, the system may continuously re-assign tasks (when it makes sense to do so and is of low risk) between users to best match the cognitive state and goal of each user. For example, James' coding tasks on a Monday did not go well and he did not complete them all; however, Tim's coding tasks were all completed successfully. Because James will be less motivated to do coding on Tuesday, the system re-assigns some coding tasks from James to Tim, and reassigns some non-coding related tasks from Tim to James. The method can therefore increase the efficiency of a team by moving tasks between members and continuously learns to match cognitive states and goals of all members of the team to specific tasks.

The planning action may take into consideration a user's history (e.g. a history of achieving a mood outcome.)

In one embodiment, the method may involve managing a person's daily goals based on the person's recent performance in completing certain of the daily goals. This may be done (and learned) for various cohorts of users, including children, adults, people with autism or ADHD, pre-Alzheimer's etc.—with an emphasis on mood shaping.

In one embodiment, a set of to-do items may be obtained in various manners. For example, a user may specify window of time. A subset of the to-do items may be automatically prioritized as candidate tasks to be performed during the specified window of time to achieve the emotional goal or cognitive goal.

As the software attempts to induce a mood, such considerations of task triage, as mentioned previously "protecting one's time" by insulation, isolation and delegation; motivational emphasis; and "recovering from bad time-habits" may be considered. Furthermore, the system can try different work styles (taken from the business and/or psychological scientific literature) for different users. That is, the system can process the specification of a user in order to determine their profile and then schedule accordingly. For example, on user may have different time allocations or scheduling than another user based on one user being a morning person and the other not.

If useful, coloration can be used to suggest emotional or cognitive characteristics of individual items, but also overall moods for a set of adjacent tasks. As the tasks are re-ordered, overall mood for part of a day or an entire day may change based on ordering of deferring of certain activities. Colors can also indicate and estimate how good a person will "feel" having achieved one or more tasks in a given time period.

In one embodiment, the inventive time-management system may take into account such factors as a particular user's response to stress (including substance abuse, chronic pain, cognitive function, depression, emotional function, headache, post-traumatic stress disorder, stomach ulcers, depression, heart disease, and the like) and use such information when planning. Thus, a lighter schedule load can be created for a user who does not respond well to stress (i.e., plan many break times) whereas a heavy load can be introduced for someone who works well under stress (e.g., user is highly stressed and pack their schedule with more tasks). In some cases, a user may actually optionally provide information on his "stress cohort" using a profile or other means.

In another embodiment, the inventive time-management system may take into account such factors as stress management and make suggestions for such stress management as part of the time management planning (e.g. exercise, music, meditation, etc.). Stress management may be automatically scheduled among tasks, depending on the task and the user. The method may learn effective or appropriate stress management auto-insertions by "observing" a user, or user cohort, in various ways (e.g. with respect to mood, task completion, etc.). Stress is not the only consideration, because other cognitive state management factors are contemplated by this invention (e.g., feeling happy, feeling more fulfilled in job, etc.).

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 2, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system, Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 2, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/sewer 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 3:
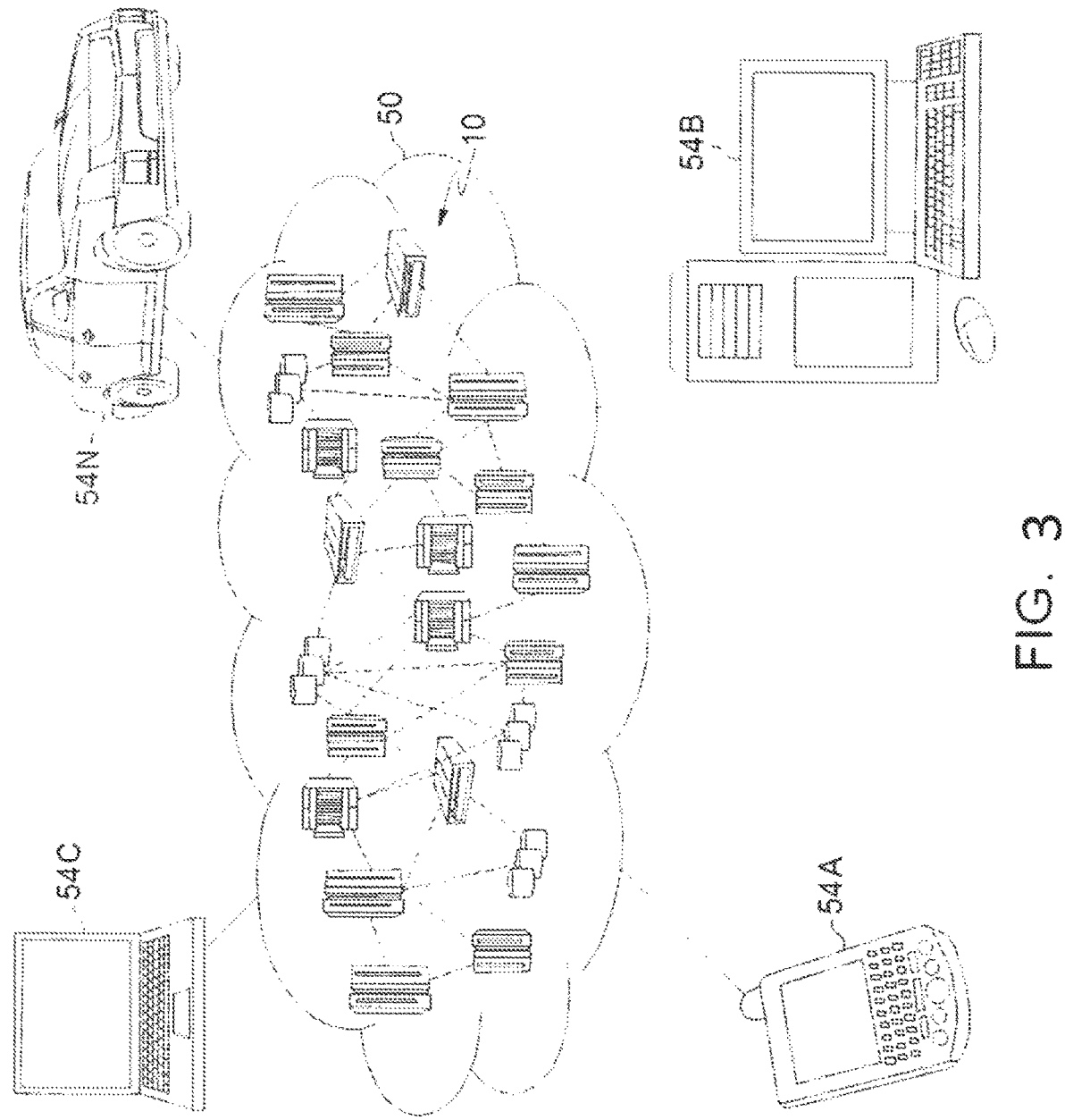
FIG. 3 depicts a cloud-computing environment 50 according to an embodiment of the present invention.

Referring now to FIG. 3, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 3 are intended to be illustrative only and that computing nodes 10 and cloud computing environment 50 can communicate with any type of computerized circuit over any type of network and/or network addressable connection (e.g., using a web browser).

Figure 4:
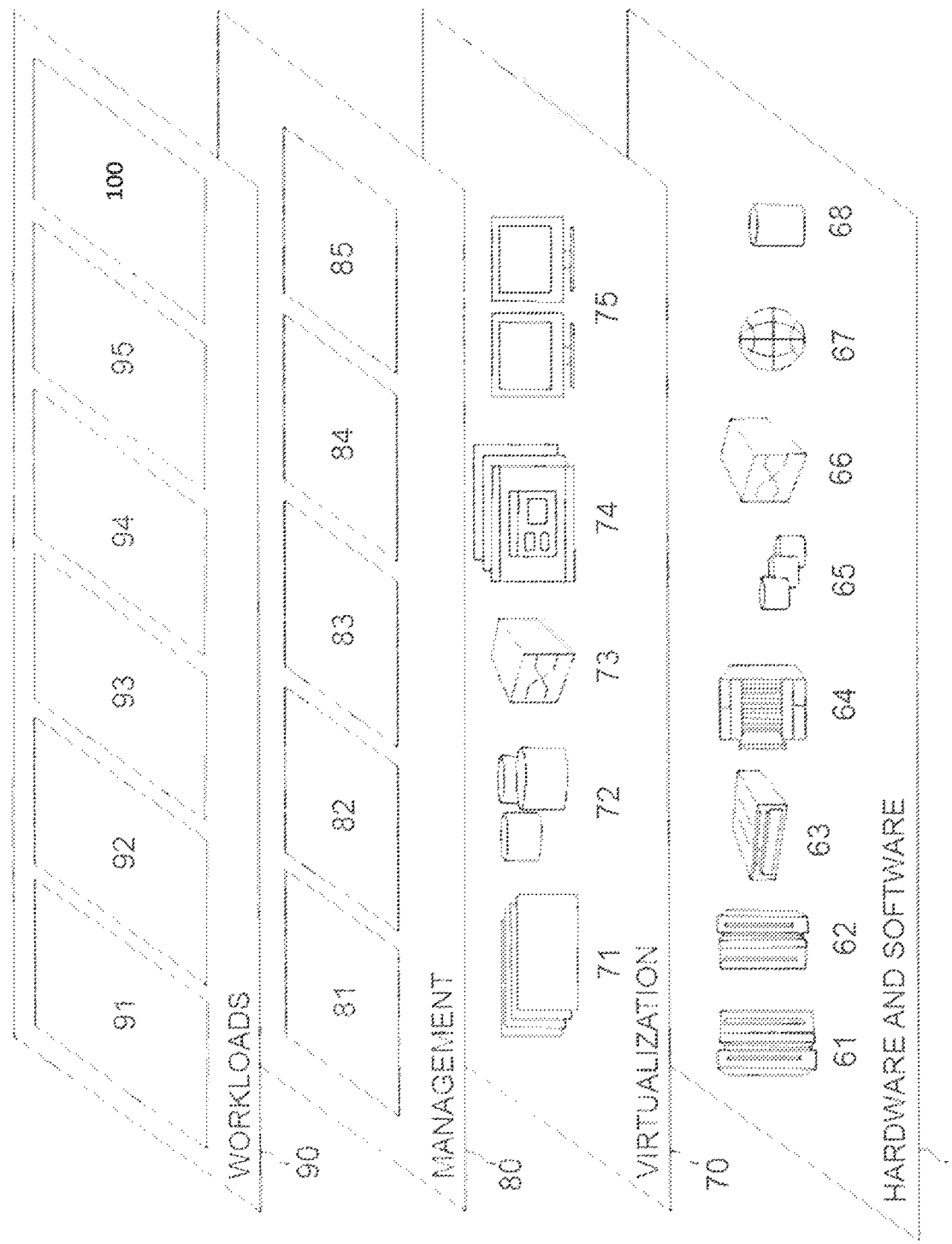
FIG. 4 depicts abstraction model layers according to an embodiment of the present invention.

Referring now to FIG. 4, an exemplary set of functional abstraction layers provided by cloud computing environment 50 (FIG. 43) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are net. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and time-management planning method 100 in accordance with the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g. light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the users computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or of diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented time-management planning method that interacts with a cloud computing environment server, the method comprising:
    determining, via a computer, a cognitive state and a contextual state of a user;
    compiling, via the computer, a specification of a cognitive goal including an anticipated cognitive state of others associated with accomplishing a scheduled task for a period of time and protected times for the period of time; and
    performing, via the computer, a planning action by executing natural language processing to nag a user, via a time management software platform interfacing with a chatbot to contact the user, to adjust the scheduled task based on the specification of the cognitive goal and the cognitive state and the contextual state of the user, the adjusting the scheduled task ignoring adjusting of the scheduled task to the protected times unless the scheduled task has an importance factor exceeding a threshold value,
    wherein a graphical-user interface is enabled with a coloration of an indicator for the user which indicates their cognitive state and contextual state,
    wherein the planning action includes recommending, specifying, ordering, and marking, via the graphical-user interface, a set of to-dos in a specified limited window of time that compete with each other for a same time and interweaving a stress management activity during the set of to-dos in the specified limited window while factoring a response to stress of the user, and
    further comprising suggesting a stress management technique based on the response to the stress of the user,
    wherein the cognitive goal includes a goal of a team including a plurality of users, and
    wherein the planning action includes adjusting a user performing a scheduled task to advance the goal of the team,
    further comprising:
        repetitively comparing, via the computer, the scheduled task and the cognitive state and the contextual state of the user;
        stopping, via the computer, the user from performing the scheduled task; and
        automatically, via a cloud on-demand self-service on the graphical-user interface that communicates with the cloud computing environment server, rescheduling on the graphical-user interface, via the computer, the scheduled task to a different time when the comparison indicates a conflict and coloring the task a different color indicating the rescheduling.

2. The computer-implemented method of claim 1, wherein the contextual state of the user includes at least one of:
    a physical environment;
    another scheduled task;
    upcoming tasks;
    a location;
    health-related information;
    an amount of recent exercise; and
    a social environment.

3. The computer-implemented method of claim 1, wherein the planning action is determined based on an outcome of a prior taken planning action.

4. The computer-implemented method of claim 1, wherein the planning action includes assigning and re-assigning scheduled tasks between team members to better match individual cognitive goals of all the team members with the overall cognitive state of the team.

5. The computer-implemented method of claim 1, wherein the planning action is determined based on an outcome of a prior taken planning action.

6. The computer-implemented method of claim 5, wherein the planning action includes assigning and re-assigning scheduled tasks between team members to better match individual cognitive goals of all the team members with the overall tasks of the team.

7. The computer-implemented method of claim 1, wherein the cognitive state factors in a stress of the user, the stress of the user being determined based on at least one of:
   substance abuse;
   chronic pain;
   cognitive function;
   depression;
   emotional function;
   a headache;
   a post-traumatic stress disorder;
   stomach ulcers; and
   a heart disease.

8. The computer-implemented method of claim 1, embodied in a cloud-computing environment.

9. A computer program product for time-management planning that interacts with a cloud computing environment server, the computer program product comprising a computer readable storage medium having program instructions embodied therewith, the program instructions executable by a computer to cause the computer to perform:
   determining, via a computer, a cognitive state and a contextual state of a user;
   compiling, via the computer, a specification of a cognitive goal including an anticipated cognitive state of others associated with accomplishing a scheduled task for a period of time and protected times for the period of time; and
   performing, via the computer, a planning action by executing natural language processing to nag a user, via a time management software platform interfacing with a chatbot to contact the user, to adjust the scheduled task based on the specification of the cognitive goal and the cognitive state and the contextual state of the user, the adjusting the scheduled task ignoring adjusting of the scheduled task to the protected times unless the scheduled task has an importance factor exceeding a threshold value,
   wherein the planning action includes recommending, specifying, ordering, and marking a set of to-dos in a specified limited window of time that compete with each other for a same time and interweaving a stress management activity during the set of to-dos in the specified limited window while factoring a response to stress of the user, and
   wherein a graphical-user interface is enabled with a coloration of an indicator for the user which indicates their cognitive state and contextual state,
   further comprising suggesting a stress management technique based on the response to the stress of the user,
   wherein the cognitive goal includes a goal of a team including a plurality of users, and
   wherein the planning action includes adjusting a user performing a scheduled task to advance the goal of the team,
   further comprising:
   repetitively comparing, via the computer, the scheduled task and the cognitive state and the contextual state of the user;
   stopping, via the computer, the user from performing the scheduled task; and
   automatically, via a cloud on-demand self-service on the graphical-user interface that communicates with the cloud computing environment server, rescheduling on the graphical-user interface, via the computer, the scheduled task to a different time when the comparison indicates a conflict and coloring the task a different color indicating the rescheduling.

10. The computer program product of claim 9, wherein the contextual state of the user includes at least one of:
   a physical environment;
   another scheduled task;
   upcoming tasks;
   a location;
   health-related information;
   an amount of recent exercise; and
   a social environment.

11. The computer program product of claim 9, wherein the planning action is determined based on an outcome of a prior taken planning action.

12. A time-management planning system, said system comprising:
   a processor;
   a cloud computing environment server; and
   a memory, the memory storing instructions to cause the processor to perform:
   determining, via a computer, a cognitive state and a contextual state of a user by:
      associating the contextual state and cognitive state with prior knowledge of both task-related productivity and performance, and moods and mood outcomes;
      predicting a particular cognitive state or a particular contextual state based on an external data source;
   compiling, via the computer, a specification of a cognitive goal including an anticipated cognitive state of others associated with accomplishing a scheduled task for a period of time and protected times for the period of time; and
   performing, via the computer, a planning action by executing natural language processing to nag a user, via a time management software platform interfacing with a chatbot to contact the user, to adjust the scheduled task based on the specification of the cognitive goal and the cognitive state and the contextual state of the user, the adjusting the scheduled task ignoring adjusting the scheduled task to the protected times unless the scheduled task has an importance factor exceeding a threshold value,
   wherein the planning action includes recommending, specifying, ordering, and marking a set of to-dos in a specified limited window of time that compete with each other for a same time and interweaving a stress management activity during the set of to-dos in the specified limited window while factoring a response to stress of the user, and
   wherein a graphical-user interface is enabled with a coloration of an indicator for the user which indicates their cognitive state and contextual state, further comprising suggesting a stress management technique based on the response to the stress of the user,
wherein the cognitive goal includes a goal of a team including a plurality of users, and
wherein the planning action includes adjusting a user performing a scheduled task to advance the goal of the team,
further comprising:
  repetitively comparing, via the computer, the scheduled task and the cognitive state and the contextual state of the user;
  stopping, via the computer, the user from performing the scheduled task; and
  automatically, via a cloud on-demand self-service on the graphical-user interface that communicates with the cloud computing environment server, rescheduling on the graphical-user interface, via the computer, the scheduled task to a different time when the comparison indicates a conflict.

13. The system of claim 12, embodied in a cloud-computing environment.

* * * * *